United States Patent
Suh (10) Patent No.: US 10,588,690 B2
(45) Date of Patent: Mar. 17, 2020

(54) ELECTROSURGICAL DEVICE

(71) Applicant: Gerald Suh, Manhasset, NY (US)

(72) Inventor: Gerald Suh, Manhasset, NY (US)

(*) Notice: Subject to any disclaimer, the term of this patent is extended or adjusted under 35 U.S.C. 154(b) by 315 days.

(21) Appl. No.: 15/794,442

(22) Filed: Oct. 26, 2017

(65) Prior Publication Data
US 2018/0116711 A1    May 3, 2018

Related U.S. Application Data

(60) Provisional application No. 62/416,347, filed on Nov. 2, 2016.

(51) Int. Cl.
| | | |
|---|---|---|
| *A61B 18/14* | (2006.01) | |
| *A61B 17/32* | (2006.01) | |
| *A61B 18/12* | (2006.01) | |
| *A61B 18/00* | (2006.01) | |
| *A61B 17/00* | (2006.01) | |

(52) U.S. Cl.
CPC .... *A61B 18/1485* (2013.01); *A61B 17/32002* (2013.01); *A61B 18/1206* (2013.01); *A61B 2017/003* (2013.01); *A61B 2017/00946* (2013.01); *A61B 2017/320004* (2013.01); *A61B 2018/00101* (2013.01); *A61B 2018/00327* (2013.01); *A61B 2018/00595* (2013.01); *A61B 2018/126* (2013.01); *A61B 2218/002* (2013.01); *A61B 2218/007* (2013.01)

(58) Field of Classification Search
CPC ........ A61B 17/32002; A61B 2017/003; A61B 2017/00946; A61B 2017/320004; A61B 18/1206; A61B 18/1485; A61B 2018/00101; A61B 2018/00327; A61B 2018/00595; A61B 2018/126; A61B 2218/002; A61B 2218/007
See application file for complete search history.

(56) References Cited

U.S. PATENT DOCUMENTS

| | | | | |
|---|---|---|---|---|
| 5,364,395 | A * | 11/1994 | West, Jr. .......... | A61B 17/32002 604/22 |
| 5,904,681 | A * | 5/1999 | West, Jr. ............ | A61B 18/1485 604/22 |
| 6,193,715 | B1 * | 2/2001 | Wrublewski ....... | A61B 18/1402 604/22 |
| 6,214,001 | B1 * | 4/2001 | Casscells ......... | A61B 17/32002 606/180 |
| 7,674,263 | B2 * | 3/2010 | Ryan .................... | A61B 18/148 606/180 |
| 2003/0216725 | A1 * | 11/2003 | Woloszko .......... | A61B 18/1402 606/41 |

* cited by examiner

*Primary Examiner* — Michael F Peffley
(74) *Attorney, Agent, or Firm* — Collard & Roe PC (57) ABSTRACT

An electrosurgical device includes a distal end region, a proximal end region and a malleable or curved shaft extending between the distal and proximal end regions. A handpiece is disposed at the proximal end region and a surgical tip with a rounded and tapered front area is positioned at the distal end region. The device includes a microdebrider. Radio frequency electrodes and bipolar electrodes are positioned at a bottom part of the distal end region spaced from the rounded and tapered front area. A heat-resistant upper surface is disposed at a top area of said surgical tip for separating the radio frequency electrodes and bipolar electrodes from overlying surface tissue.

3 Claims, 13 Drawing Sheets

ELECTROSURGICAL DEVICE

CROSS REFERENCE TO RELATED APPLICATIONS

This application is the non-provisional application of and claims benefit under 35 USC § 119(e) of U.S. Provisional Application Ser. No. 62/416,347 filed on Nov. 2, 2016, the disclosure of which is hereby incorporated by reference.

BACKGROUND OF THE INVENTION

1. Field of the Invention

The present device related generally to medical devices for cutting, evacuating and/or performing work on tissue in various regions of a patient's body.

2. The Prior Art

According to the Centers for Disease Control and Prevention (CDC), as of January 2015, in the U.S., about 12.1% of adult population or 28.5 million people suffer from chronic sinusitis, making it a more prevalent disease than diabetes and asthma. Also, chronic sinusitis is one of the ten medical conditions which contributes to 8.6 billion dollars of direct healthcare costs in the U.S. Every year, around 500,000 sinus surgeries (operating room) are performed in the U.S. Thus, the high prevalence of sinusitis is one of the major factors that will further increase the demand for ENT surgical devices, thereby driving the growth of North American ENT device market.

Moreover, according to the National Healthy Sleep Awareness Project, obstructive sleep apnea now afflicts at least 25 million adults in the U.S. Data previously published in the American Journal of Epidemiology shows that the estimated prevalence rates of obstructive sleep apnea have increased substantially over the last two decades, most likely due to the obesity epidemic. It is now estimated that 26 percent of adults between the ages of 30 and 70 years have sleep apnea.

Accordingly, there is a need for a device which can easily be used in an office or operating room setting for most minimally invasive nasal and sinus procedures as well as sleep apnea or snoring procedures involving the soft palate and tongue base. Use of such a device for adenoid or tonsil surgery would most likely be limited to the operating room setting.

In addition, there is a need for a device to address the significant need in sleep apnea surgery to develop procedures that are more effective than simple radio frequency reduction of the soft palate and tongue base, but less invasive and less morbid than the traditional UPPP as well as partial glossectomy, for those patients who are unable to tolerate or benefit from CPAP or oral appliance therapy (OAT).

SUMMARY OF THE INVENTION

A device according to an embodiment of the invention a versatile, multi-purpose, go-to device that combines the functions of a micro-debrider, a radio frequency (RF) generator, and a bipolar cautery in one. It can be used for maximal soft tissue removal as well as reduction anywhere in the upper airway from the nasal cavity (turbinates, polyps), nasopharynx (adenoid), oropharynx (palatine tonsils, soft palate), as well as hypopharynx (tongue base, lingual tonsils).

The device can have a flexible, malleable tip to allow for optimal access to diverse anatomic locations. In addition, the microdebrider and RF function may be activated simultaneously or the same device may be used with just the microdebrider, RF, or bipolar activated functions to address different surgical situations depending on purpose and anatomic sites without changing multiple hand-pieces, thereby allowing for improved operative efficiency. The same irrigation fluid can also be used for both the microdebrider to flush out the removed tissue as well as for the RF electrodes to create a controlled field to allow for improved conduction of the RF current.

A surgical device according to an embodiment of the invention combines the functions of radio frequency, microdebrider, and bipolar cautery in one malleable unit. The device results in increased efficacy as it provides maximal soft tissue reduction within the target region by combining radio frequency for long-term soft tissue volume reduction and micro-debrider for actual soft tissue removal. A combined radio frequency-micro-debrider device, by allowing for both maximal soft tissue removal as well as reduction, provides a greater clinical impact in numerous different applications, including but not limited to a variety of upper airway procedures from the nose down to the larynx. Furthermore, a device according to an embodiment of the invention provides increased versatility, so an operator can choose to use radio frequency and microdebrider in combination or radio frequency and microdebrider separately. These usages depend on anatomical location and patient characteristics. The malleable hand-piece allows for optimal placement of the device to address multiple different anatomical sites.

A surgical device according to an embodiment of the invention is applicable in multiple different anatomical sites including the nose (nasal turbinates, nasal polyps, adenoids) and throat (palate, tongue, tonsil) and many other sites. By combining the functions of a micro-debrider and radio-frequency and given its malleability, the device is cost-effective and provides for increased operative efficiency. Thus, there is no need to use or change multiple different surgical devices, or different straight or angled hand-pieces for different anatomical sites. The device of the invention, depending on the anatomic location, can also be used with just the microdebrider, radio frequency, or bipolar activated functions to address different anatomic sites, which would also allow for improved operative efficiency.

BRIEF DESCRIPTION OF THE DRAWINGS

Other benefits and features of the present invention will become apparent from the following detailed description considered in connection with the accompanying drawings. It is to be understood, however that the drawings are designed as an illustration only and not as a definition of the limits of the invention.

In the drawings, wherein similar reference characters denote similar elements throughout the several views.

DETAILED DESCRIPTION OF THE INVENTION

Figure 1:
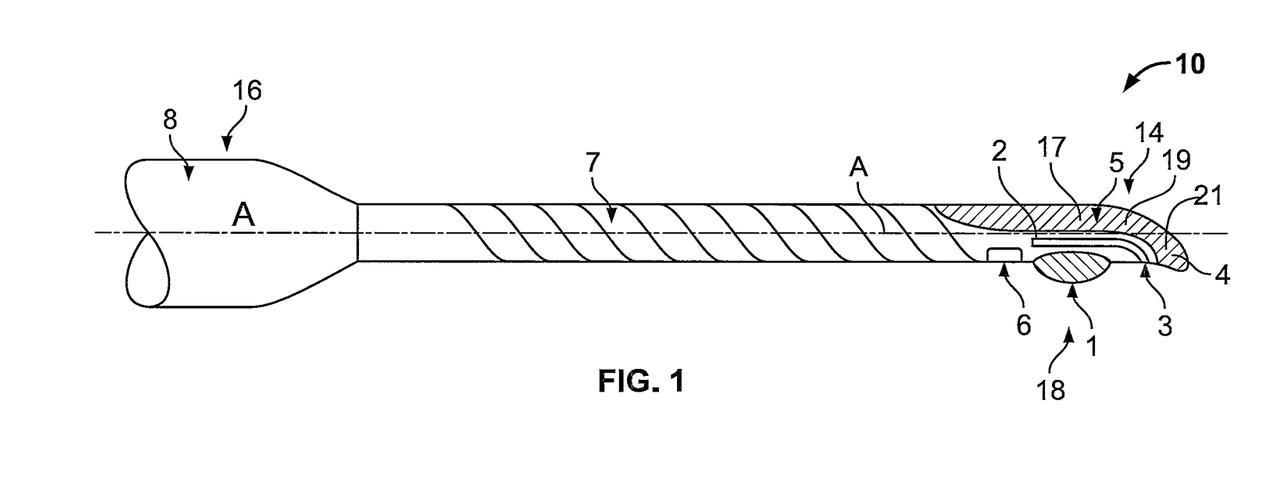
FIG. 1 is a side elevational view illustrating a front distal area of an electrosurgical device according to an embodiment of the invention.
Figure 2:
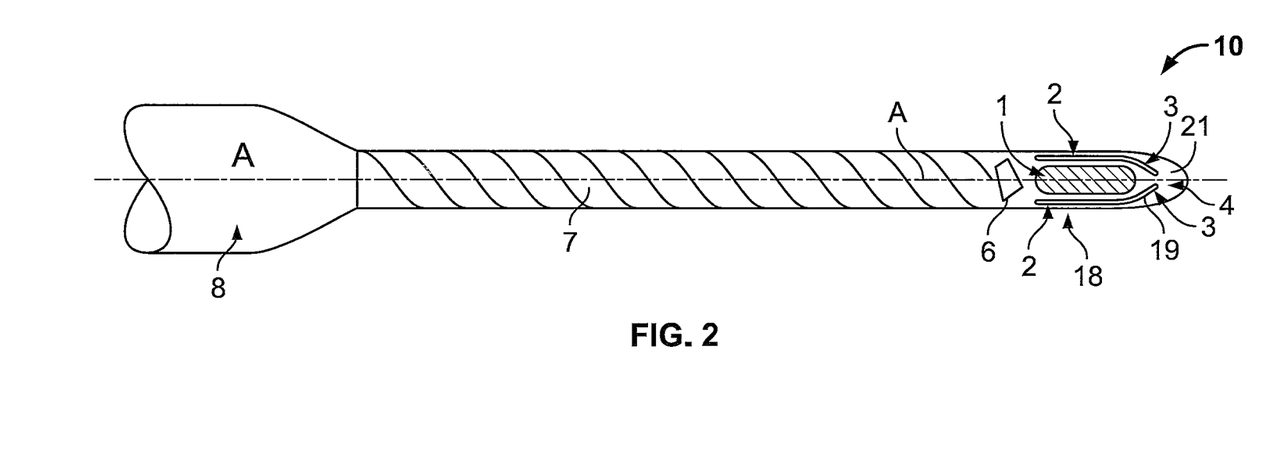
FIG. 2 is a bottom plan view thereof.
Figure 3:
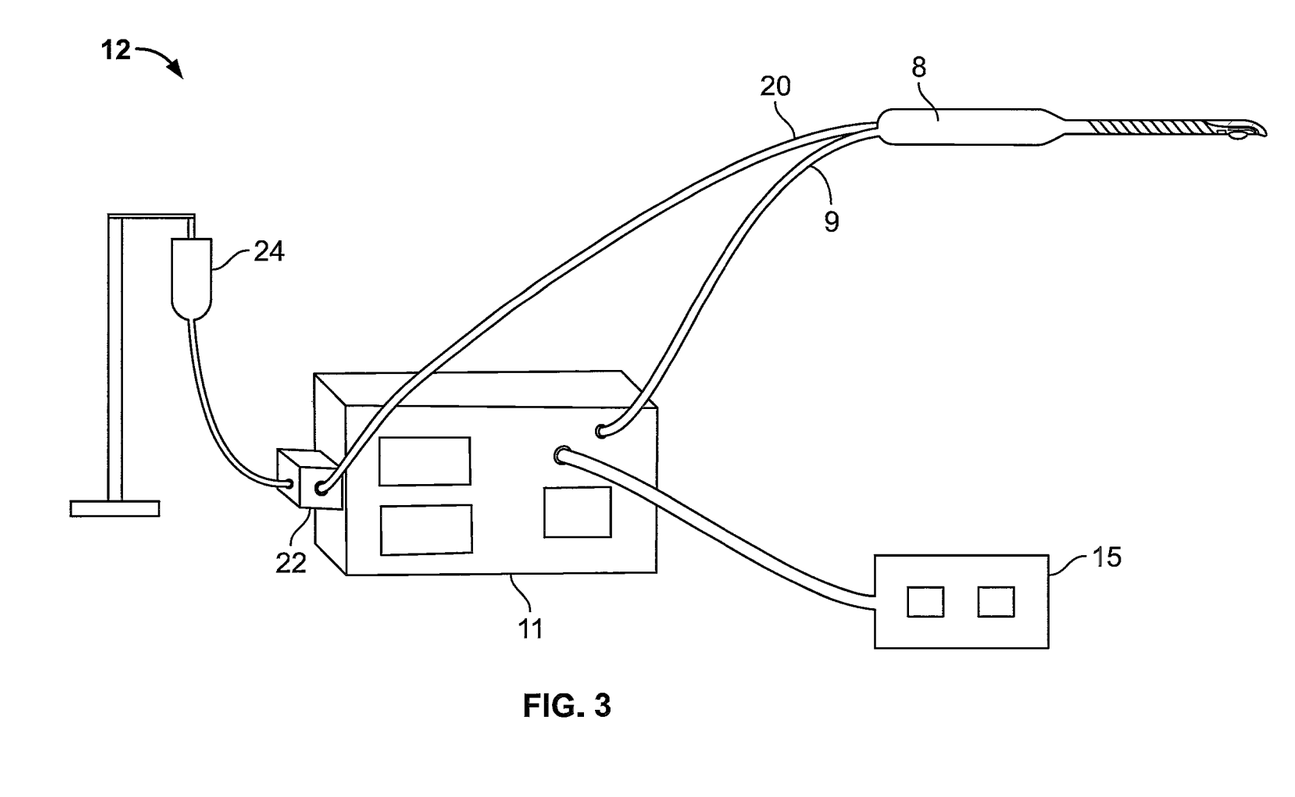
FIG. 3 is a view illustrating a system according to an embodiment of the invention.

FIGS. 1, 2 and 3 illustrate a device 10 and a system 12 according to the present invention. The device 10 is formed having a distal end region indicated generally at 14 and a proximal end region indicated generally at 16, with a shaft 7 extending therebetween. A malleable hand-piece 8 is disposed at the proximal end region and a surgical tip arrangement 18 is positioned at the distal end 14. In a device specifically applied to nose and throat surgery, the tissue resecting device utilized is referred to as a microdebrider 1. It should be noted however that the system and device of the invention are also applicable to gynecological surgery, spinal surgery and many other applications.

It will be discussed below that the essential elements/components of the invention such as a microdebrider 1 and the multiple combined unitary radio frequency-bipolar electrode assemblies 19, including radio frequency electrodes 1 and bipolar electrodes 3 are strategically positioned at the distal end 14 of the surgical tip arrangement 18. Furthermore, these elements are positioned at a bottom part of the distal end region 14, spaced from the rounded and tapered front area 4 of the tip 18. To prevent ulcerations and damage to the overlying anatomical lining, a heat-resistant upper surface 17 is formed at the top of the tip separating/isolating the electrode assemblies 19 from the surrounding tissue. This arrangement maximizes the effectiveness in removing tissue and creates maximal shrinkage of soft tissues around an operated area. In situations where tissues reduction is important, the way the electrodes are arranged creates a field surrounding the electrodes and the electrode assemblies to allow for the most tissue reduction.

The electrodes in general and bipolar electrodes 3 in particular are separated from the rounded and tapered front area 4 of the tip 18 by a space 21. In this manner, damage to the surrounding soft tissue during a surgical procedure is further minimized. The rounded and tapered front end 4 of the tip 18 allows for blunt dissection to raise the overlying mucosa and sub-mucosa, to also minimize trauma. The front area 4 of the tip 18 is heat-resistant to minimize conduction of energy to the mucosal surface and contributes to decreased surrounding tissue damage and potentially decreases a patient recovery after a surgery.

The shaft 7 accommodates the components of both the microdebrider 1 and the combined electrode assemblies 19 within its inner substantially hollow core. The hollow inner core is formed with channels which accommodate electrical current wires 40, irrigation tubing, as well as the rotor for the microdebrider 1. A central suction channel passing through the core removes soft tissue debris and blood. The shaft 7 is malleable, so it can be adapted for various application of the surgical device. The inner core dimensions of the shaft 7 are typically within the range of 2.8 mm-3 mm. This range is large enough to allow adequate removal of tissue generated during the surgical procedure by the microdebrider 1, so that the suction apparatus is not clogged, but small enough to minimize trauma to the surrounding tissues.

The hand-piece 8 adapted to control the surgical tip arrangement 18 allows for maximal flexibility and optimal positioning to address multiple anatomical locations and variability in different patients' anatomies. The hand-piece 8 can be either integrated with the surgical tip 18, so as to be completely disposable or may be re-useable with an attached disposable tip. According to one embodiment of the invention, an integrated hand-piece 8 is provided, where the hand-piece 8 and the surgical tip 18 are integrated in one inseparable unit. In this embodiment, the hand-piece 8 and the surgical tip 18 are disposed after each application. In another embodiment, the surgical tip 18 is detachable from the hand-piece 8. Since the hand-piece 8 is reusable, only the detachable surgical tip 18 is replaced after each application.

The microdebrider 1 is a rotary cutting tool with a blade that spins around a hollow metal tube provided for cutting out a tissue and is coupled to a source of suction. The blade is driven by a motor housed within the hand-piece 8 that rotates an inner shaft which extends from the hand-piece 8 to the blade tip. In this manner, during a surgery, a tissue is being cut out by the microdebrider 1 and removed simultaneously through a suction port 6 disposed in the close vicinity thereof. As illustrated, the microdebrider 1 is efficiently positioned at the bottom distal area of the surgical tip arrangement 18. This location enables the operator to properly manipulate the tool and prevent cutting through the lining in to the skin.

As specifically illustrated in FIGS. 1 and 2, to desiccate and simultaneously shrink a tissue, two radio frequency electrodes 2 are provided, which radio frequency electrodes extend laterally/longitudinally on both sides of the microdebrider 1. As more specifically illustrated in FIG. 2, the radio frequency electrodes 2 are symmetrical with respect to the microdebrider 1. Once the tissue is removed by the microdebrider 1, an operator is able to treat the operated area through the use of the electrodes symmetrically on both sides and at the respective depths by applying a low frequency current to avoid unnecessary damage to surrounding tissue.

As illustrated in FIGS. 1 and 2, in the longitudinal direction, each radio frequency electrode 2 extends laterally along a longitudinal axis of the surgical tip 18 and along the length of the microdebrider 1. The bipolar electrodes 3 extend at an angle to a front part of the respective radio frequency electrodes 2 and are used primarily when cauterization is needed. As shown in the side elevational view of the FIG. 1, the radio frequency electrode 2 extends along the longitudinal axis A-A of the tool and disposed above the microdebrider 1. The respective bipolar electrode 3 extends at an angle to the front portion of the radio frequency electrode 2 in the downward direction. The bipolar electrodes 3 positioned at the front area of the surgical tip 18 allow for precise visualization and targeted cauterization of affected vessels, with less trauma to the surrounding tissues. This position of the bipolar electrodes 3 enables a device according to an embodiment of the invention to better target the vessels affected by the surgical procedure.

In one embodiment of the invention, each radio frequency electrode 2 and the respective bipolar electrode 3 form a combined unitary electrode assembly 19. As shown in FIG. 2, multiple electrode assemblies 19 practically surround the microdebrider 1 in general and a front portion thereof in particular. In the combined unitary radio frequency-bipolar electrode assemblies 19, the same feed for the electrical current is used for the radio frequency electrodes 2 and the bipolar electrodes 3. Thus, the electrical connection to the device is simplified and is more efficient compared to the arrangement with two separate electrodes.

Radio frequency ablation is a medical procedure where dysfunctional tissue is ablated or reduced using heat generated from a high frequency alternating current (usually in the range of 350-500 kHz). The radio waves do not directly simulate nerve or muscle, and minimize collateral heat damage compared to mono-polar or bipolar cautery. The amplitude of the radio frequency wave is adjustable via a power unit 11 or foot-pedal 15.

In an embodiment of the invention, in order to achieve the radio frequency function, an operator uses a lower heat range by pressing one panel in a control block. In this manner, the radio frequency electrode 2 generates/provides electrical current having the above mentioned low frequency range. By pressing a different panel, a bipolar function is activated at the electrode 3 disposed at front area of the unitary electrode assemblies 19, thereby achieving a higher frequency and higher temperature ranges that cauterize any open blood vessels.

A beneficial feature of an embodiment of the invention is the provision of the microdebrider 1 surrounded by the multiple combined unitary radio frequency-bipolar electrode assemblies 19. By the arrangement, the effect of the surgical treatment provided by the medical device of the invention is enhanced both by removing tissue with the microdebrider 1, whereas with radio frequency a soft tissue shrinking or reduction is simultaneously achieved.

The microdebrider 1 and the radio frequency electrodes 2 are adapted for dual functionality. In a preferred functionality, these elements are used together in one step of a surgical procedure. A control unit is programmed, so that one position of a control foot pedal 15 activates both elements. In another application, the microdebrider 1 and the electrodes are adapted for separate and independent use. In this application the radio frequency 2 and the bipolar 3 electrodes are adapted to be used separately from each other.

Although the use of the two electrode assemblies 19 in the surgical tip 18 has been discussed above, an arrangement having an array of multiple (more than two) electrode assemblies is also contemplated within the scope of the invention. In the array, similar to the above-discussed embodiments, the radio frequency electrodes 2 are positioned laterally, longitudinally with respect to the microdebrider 1 and inferiorly at the surgical tip. This arrangement provides maximal soft tissue penetration circumferentially around the active electrodes, especially centrally, laterally and deep, while maintaining exposure to a superficial, overlying mucosa. Lateral positioning of the radio frequency electrodes 2 in the array is also desired to prevent any blockage of the centrally positioned microdebrider core.

Referring now to FIG. 3, illustrating a system 12 according to an embodiment of the invention, the system 12 includes a power source connector 9 and a fluid source connector 20 for connection to a fluid source, which can be combined with a suction source connector. Tissue fragment and fluids can be removed from a surgical site through the port 6 in the distal end region 14 via the suction source. The same irrigation fluid is used for both the microdebrider 1 to flush out the removed tissue, as well as for the electrodes assemblies 19 to create a controlled field and provide for improved conduction for the radio frequency electrical current. The latter enables a device according to an embodiment of the invention to maximize the effect of the radio frequency at the surgical tip 18.

As illustrated in FIG. 3 the hand-piece 8 is attached to a power unit 11 via the connector 9, which is connected to a foot pedal 15 that activates various functions/components of the surgical device 10 including the surgical tip 18. The hand piece 8 is also connected by a fluid source connector 20 or irrigation tubing to a flow control unit 22 for controlling the flow of the irrigation fluid. The flow-control unit 22 controls the amount of fluid irrigation, such as saline, delivered to the surgical tip 18. Although, the flow control unit is shown to be attached to the power unit 11, it can also be provided as a separate aggregate. An IV solution bag 24 contains saline fluid which is directed to the flow control unit 22 and to the hand piece 8.

Figure 4:
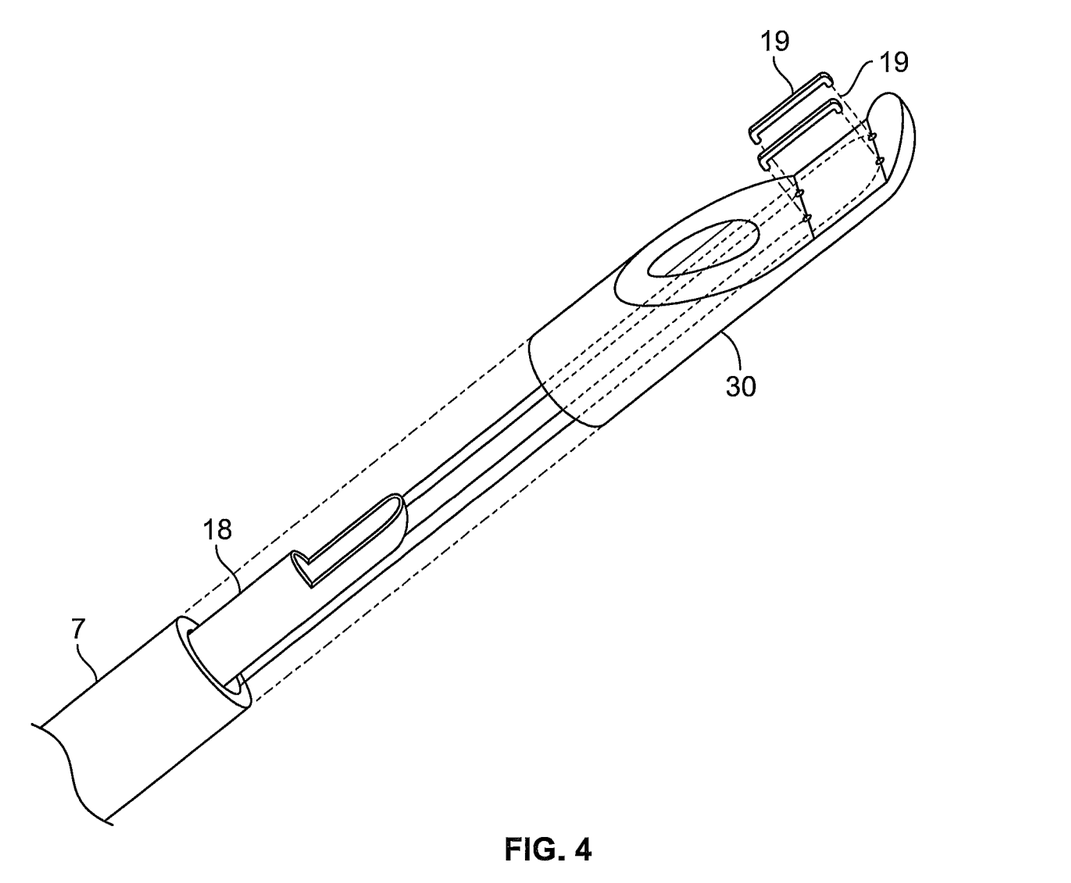
FIG. 4 is an exploded view illustrating an outer sheath separated from the microdebrider tip.

FIG. 4 is an exploded view illustrating an outer sheath 30 separated from the microdebrider tip 18 and also showing position of the radio frequency electrodes or wires 2. The initial embodiment of the invention shows the radio frequency wire 2 incorporated within the outer shaft 7 extending from the hand-piece to the device tip 18. However, another embodiment shows a sheath 30 housing the radio frequency array adapted to be positioned over the device tip. The electrodes are disposed at one side of the tip accommodating the treatment area and pass through the tip back to the other side of the device. In actuality, FIG. 4 illustrates the initial embodiment of the invention, with the active electrodes being substantially parallel to the shaft 7. However, another embodiment with the active electrodes being substantially perpendicular to the shaft is also within the scope of the invention. In the latter case, an operator is able to bring the active electrodes closer to the microdebrider, so as to further improve the efficiency of the device. FIG. 4 shows the sheath 30 adapted to be positioned over the microdebrider tip 18. In the assembled condition (see FIGS. 5 and 7-9) the hollow microdebrider core is position within the interior of the device, extends through the sheath 30, and appear at the distant end to facilitate cutting the tissue.

Figures 5, 6:
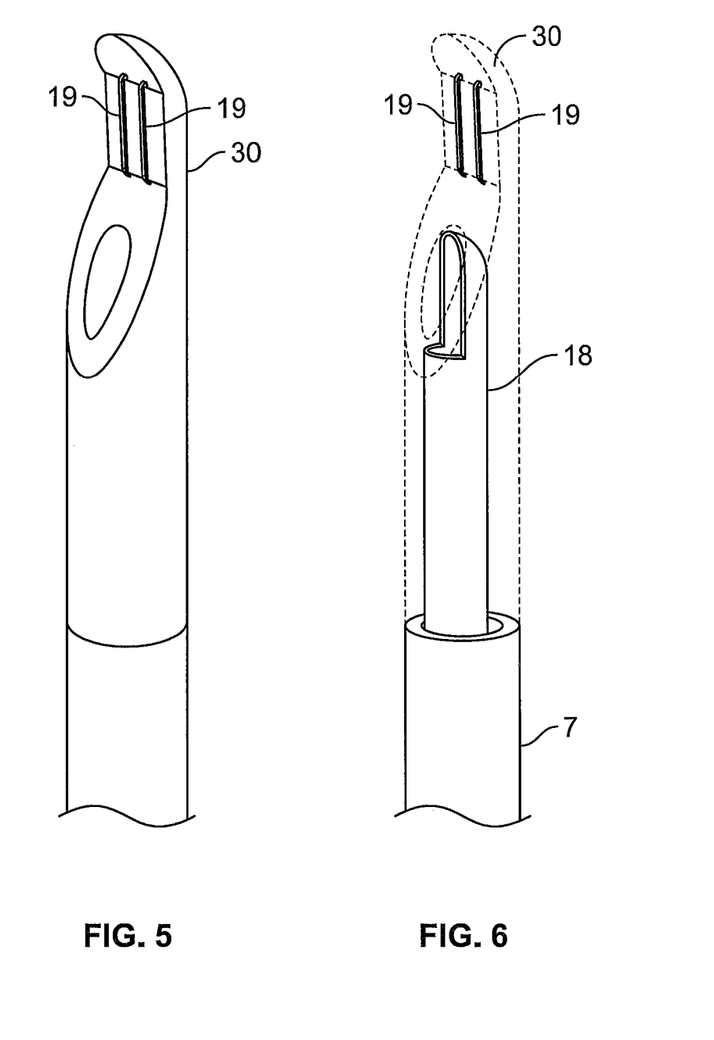
FIG. 5 is an assembled view of the FIG. 4 embodiment.
FIG. 6 illustrates the inner core of the microdebrider.

FIG. 5 is an assembled view of the FIG. 4 embodiment showing the sheath 30 positioned on the microdebrider.

FIG. 6 illustrates the inner core of the microdebrider, with the outer sheath 30 in shadow showing how it is fit at the distal end of the inner core.

To summarize the above, FIG. 4 is an exploded view of the device of the invention illustrating an interface between the microdebrider 1 and the outer sheath 30. FIG. 5 is the assembled view of the front portion of the device illustrating the sheath 30 being positioned on the core body. FIG. 6 is another illustration of the microdebrider, which is also depicted in FIG. 4.

Figure 7:
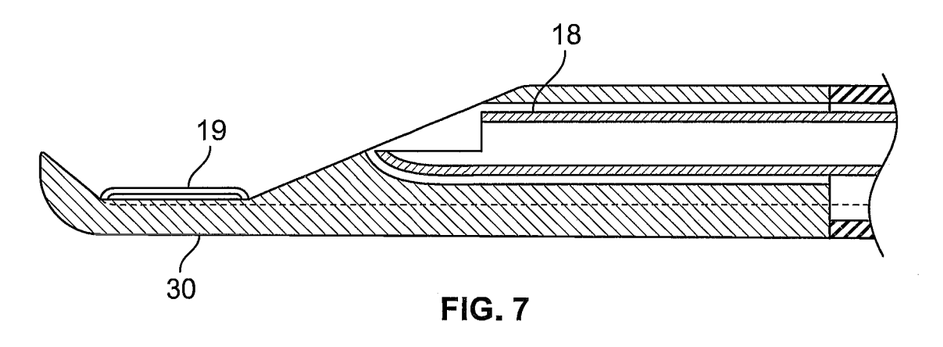
FIG. 7 is a cross-section view showing the relationship of the hollow inner core of the microdebrider tip to the electrodes.

FIG. 7 is a cross-section view showing the relationship of the hollow inner core of the microdebrider tip 18 in relationship to the electrodes exiting from the tip of the distal area of the device. This view shows that the electrodes are spaced from the tip of the microdebrider. It should be noted however, that the preferred embodiment the active radio frequency electrodes 2 are positioned closer to the microdebrider tip. The tip is beveled to allow for easier dissection of the soft tissue.

Figure 8:
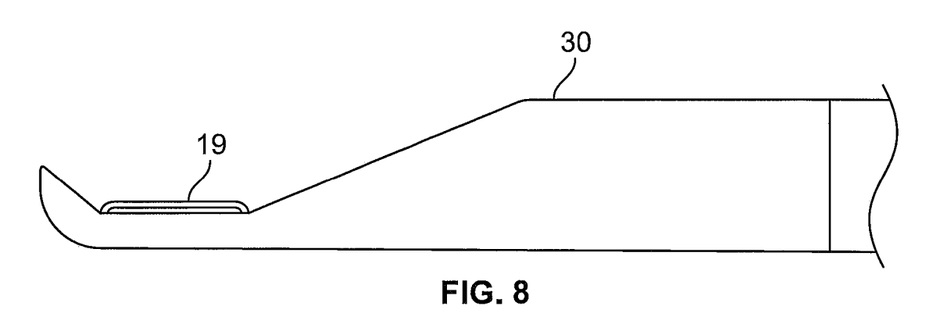
FIG. 8 is a side elevational view showing the outer core of the tip and the inner core.

FIG. 8 is a side elevational view, similar to that of FIG. 7 and showing the outer core of the tip. This view also shows the inner core of the microdebrider 1.

Figure 9:
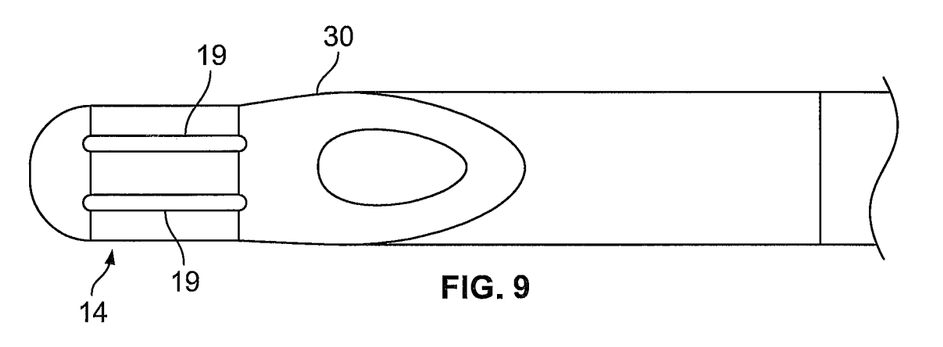
FIG. 9 is a bottom view of the tip showing the hollow core and the electrodes.

FIG. 9 is a bottom view of the tip showing the hollow core of the microdebrider and the electrodes exiting from the tip at the distal, active end 14 of the device.

Figure 10:
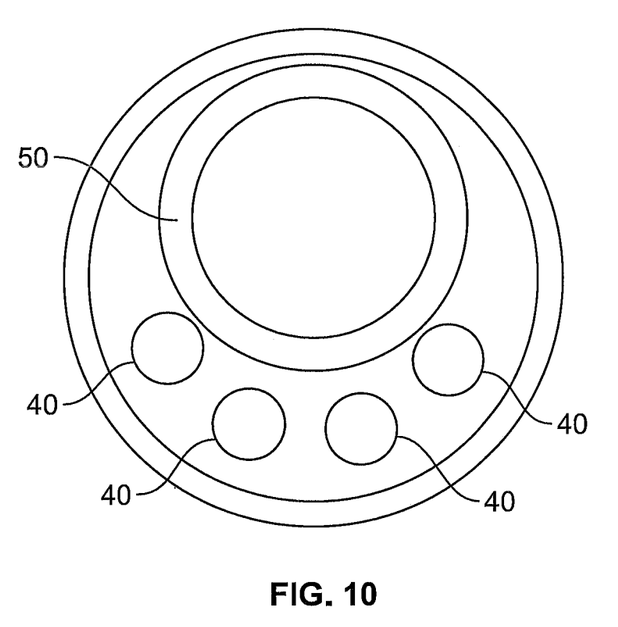
FIG. 10 is a cross section view illustrating the hollow inner core of the microdebrider shaft in relationship to the electrodes.

FIG. 10 is a cross-section view illustrating the hollow inner core of the microdebrider shaft in relationship to the electrodes passing through the shaft of the device.

Figure 11:
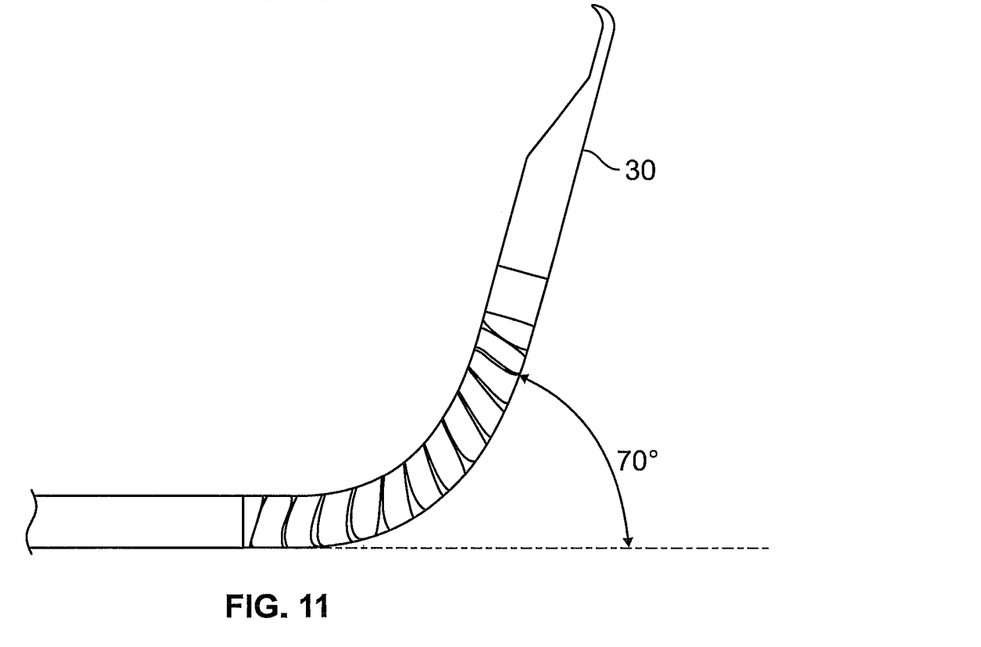
FIG. 11 shows how flexible tip of the device is.

FIG. 11 shows how flexible the tip of the device is, so it can be used for treatment of different areas of a patient body. According to this figure, the tip can be flexed beyond 70 degrees in either direction. This is an illustration of one embodiment of forming the flexible or malleable tip of the device, whereas the inner and/or outer shaft are scored circumferentially in set increments or sequentially, which allows the shaft to the bent in multiple different directions.

Figure 12:
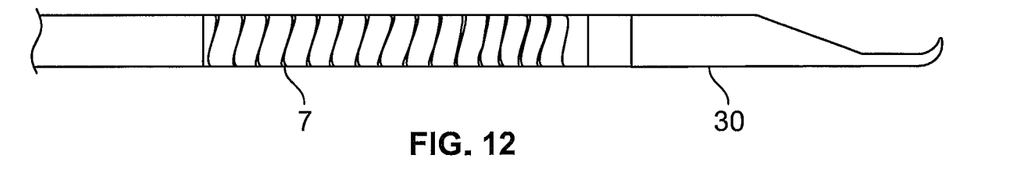
FIG. 12 is a view similar to FIG. 11, but showing the tip in its normal extended position.

FIG. 12 is a view similar to FIG. 11, but showing the tip in its normal, extended position.

Figure 13:
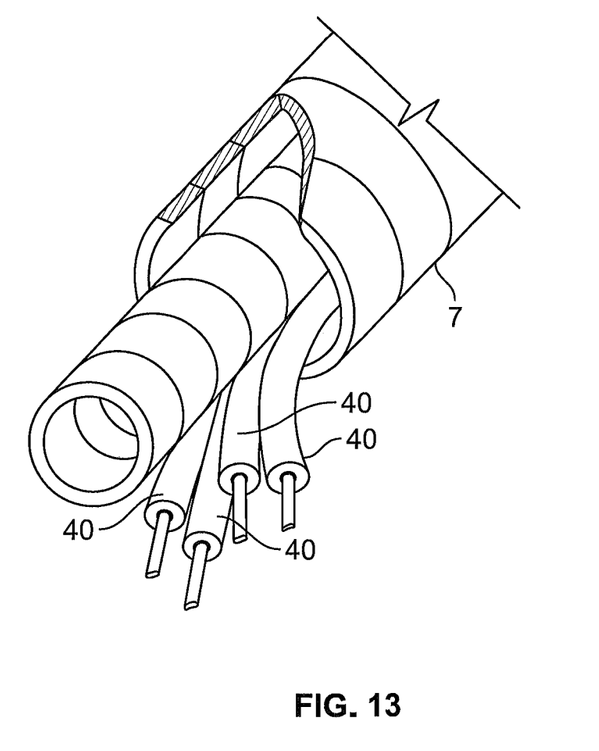
FIG. 13 is a more complete depiction of the inner core.

FIG. 13 is a more complete depiction of the inner core of the shaft 7 of the device, showing the hollow cored of the microdebrider 1 positioned within the malleable tip. The electrodes are also shown in their relationship to the shaft.

Figure 14:
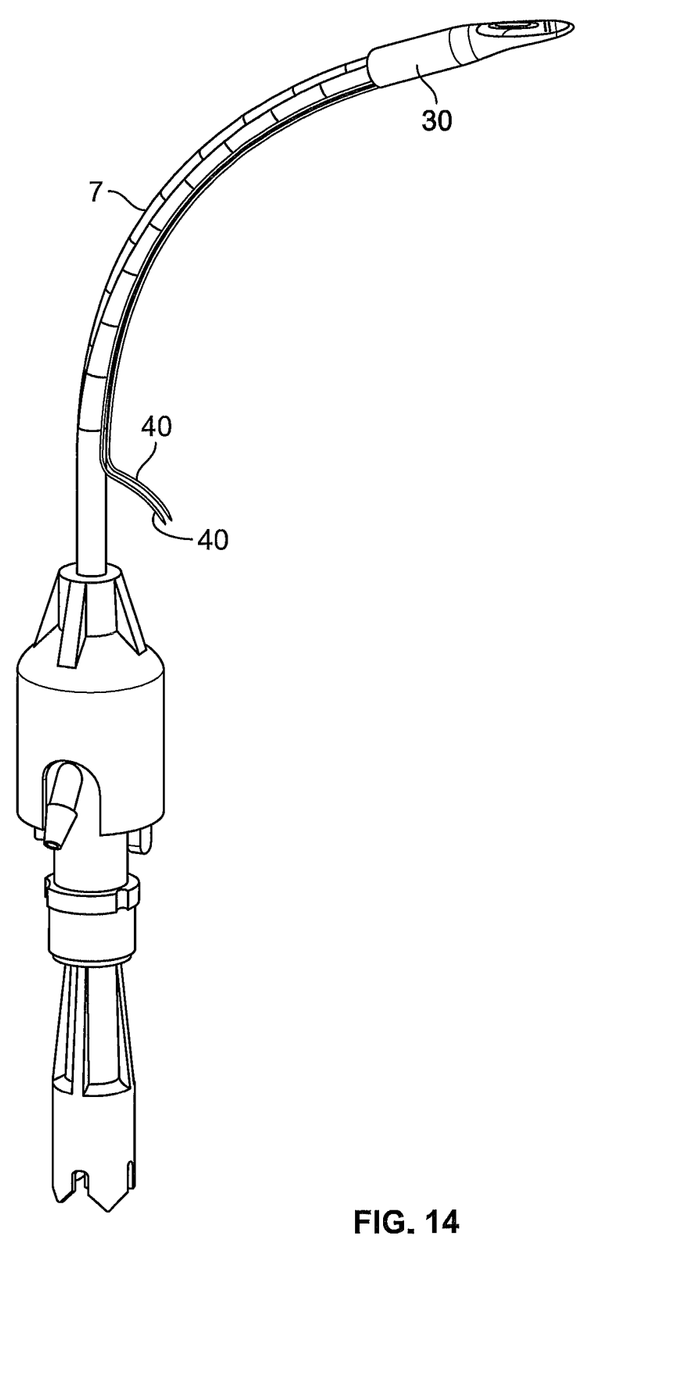
FIG. 14 is an isometric view of the tip of the device in its flexed position.

FIG. 14 is an isometric view of the tip of the device in its flexed position, showing the active electrodes as well as the position of the microdebrider tip at the distant end. This is the depiction of one embodiment of the invention, with the electrodes disposed at the exterior of the shaft 7. In an alternate embodiment the active electrodes are housed within the core of the tip of the shaft 7.

Figure 15:
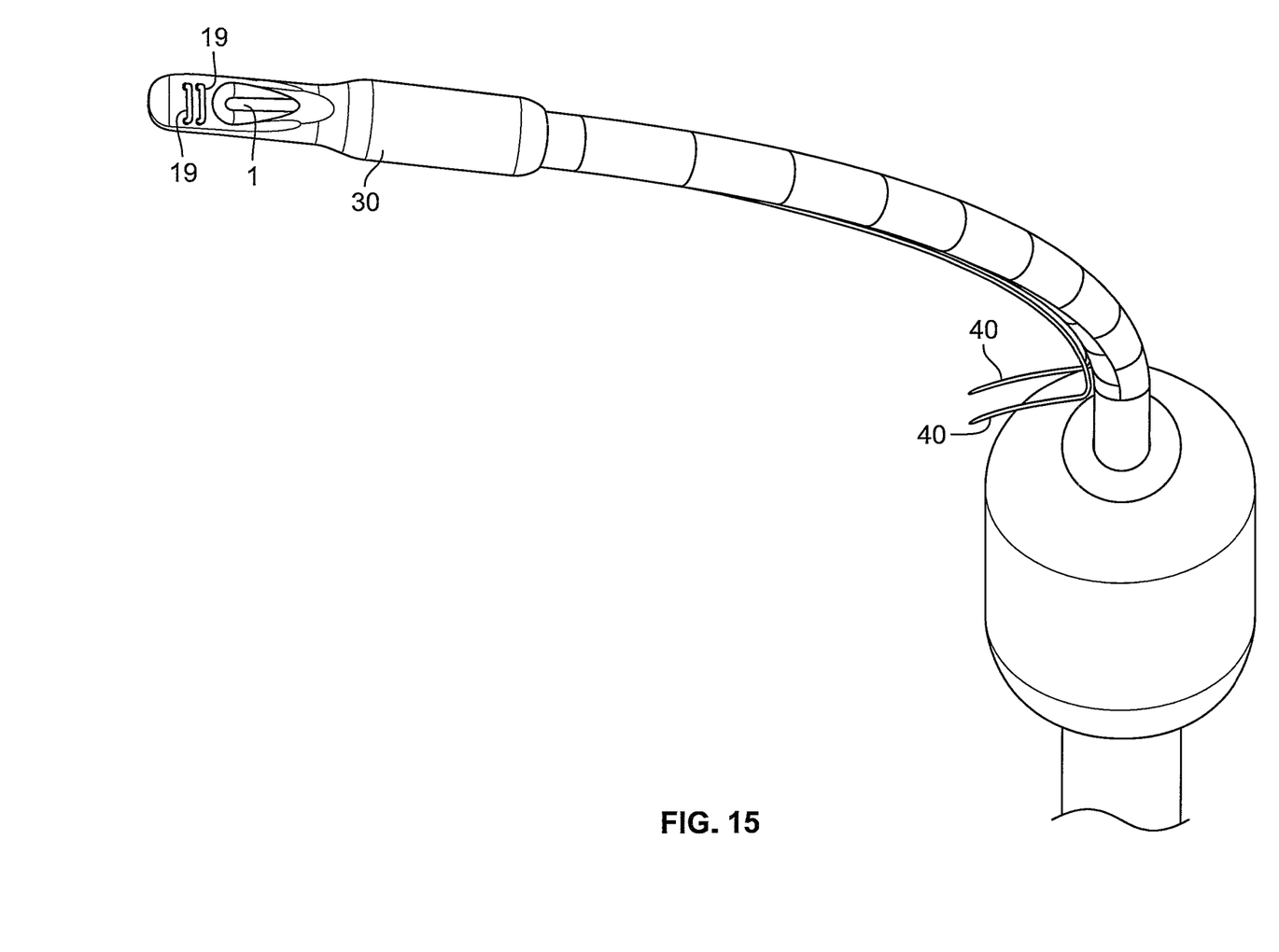
FIG. 15 is a bottom view of the tip of the device in the flexed position.

FIG. 15 is a bottom view of the tip of the device in the flexed position.

Figure 16:
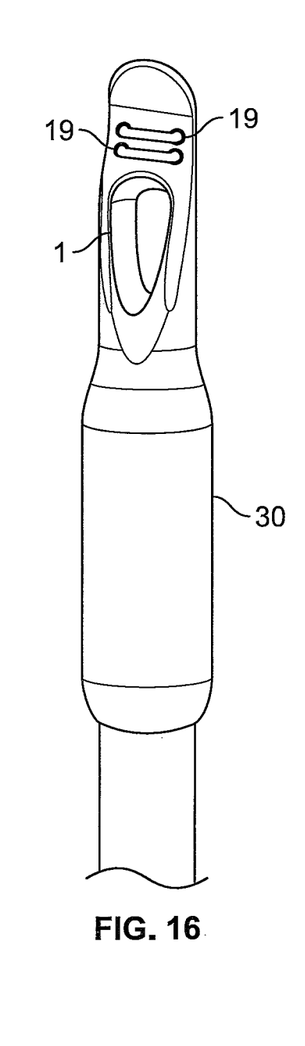
FIG. 16 is an enlarged, detailed bottom view of the tip illustrating the relationship of the microdebrider in the open position relative to the electrodes.

FIG. 16 is an enlarged, detailed bottom view of the tip illustrating relationship of the microdebrider in the open position, relative to the electrodes 2 disposed substantially perpendicular to the shaft.

Figure 17:
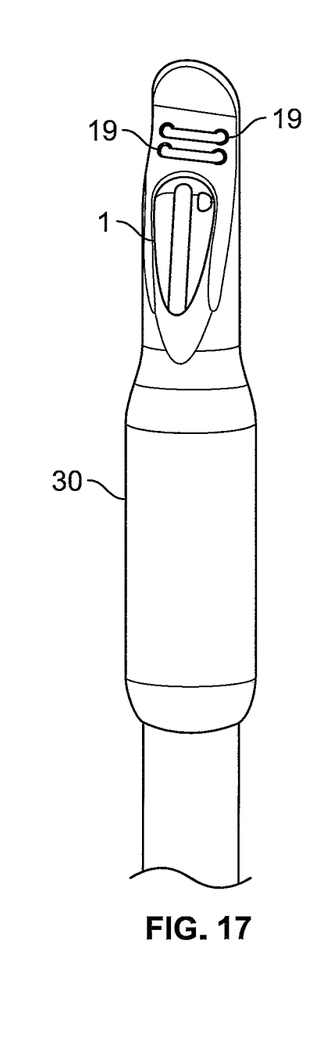
FIG. 17 is a similar view of FIG. 16, but showing the microdebrider tip in a partially closed position used for cutting tissue.

FIG. 17 is a similar view of FIG. 16, but showing the microdebrider tip in a partially closed position used for cutting the tissue. The radio frequency electrodes 2 are positioned perpendicular to the shaft.

Figure 18:
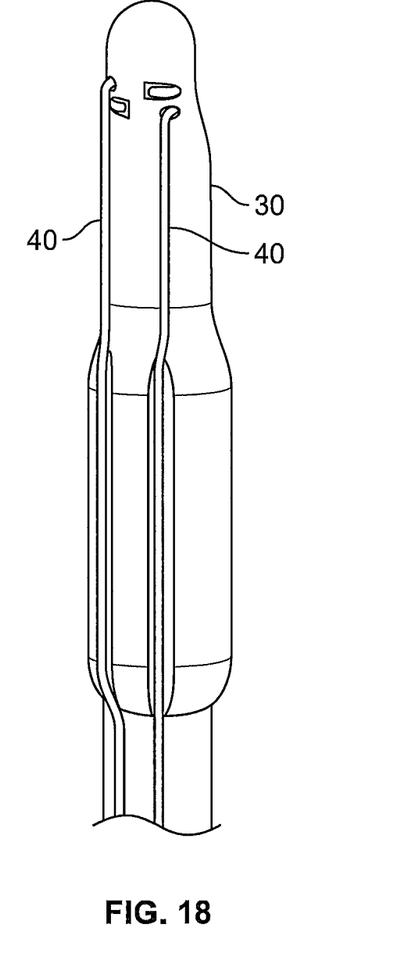
FIG. 18 is a rear view of the sheath shown in FIG. 4.

FIG. 18 is a rear of the sheath 30 shown in the FIG. 4. The electrodes or wires shown in FIG. 4 are not exposed in the actual device and are covered by the sheath illustrated in various figures of the application, including FIG. 17. As illustrated, only the active electrodes on the side opposite to the operational area of the device are exposed.

Figure 19A:
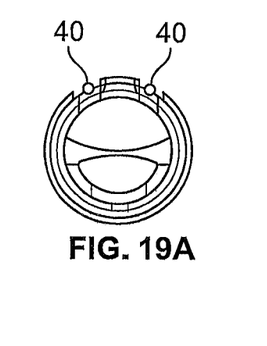
FIG. 19A is an end view of the tip.
Figure 19B:
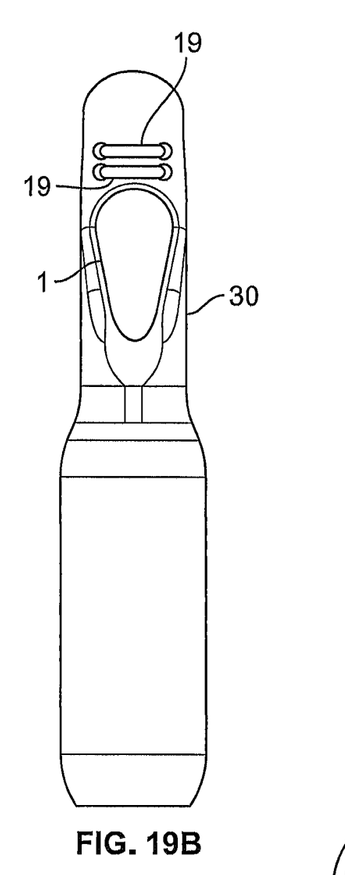
FIG. 19B is a bottom view of the tip.
Figure 19C:
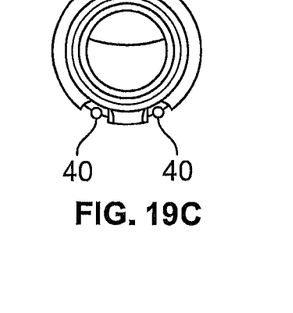
FIG. 19C is another end view of the tip.
Figure 19D:
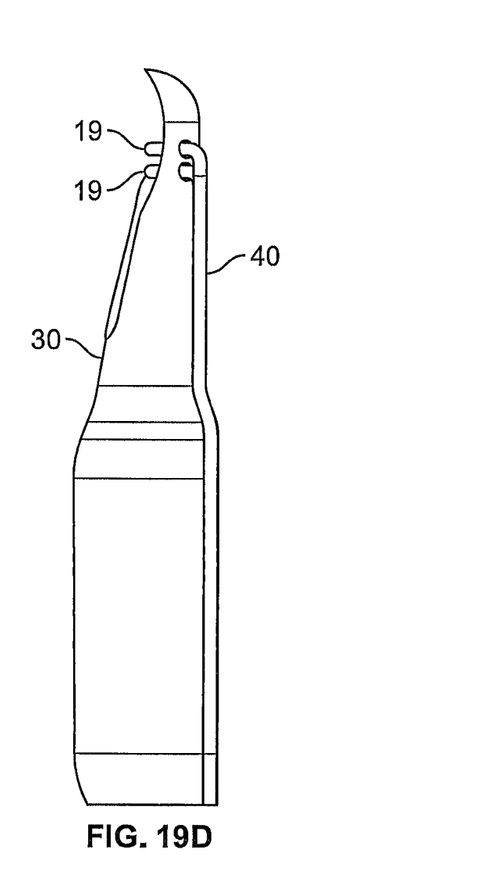
FIG. 19D is a side elevational view of the tip.
Figure 19E:
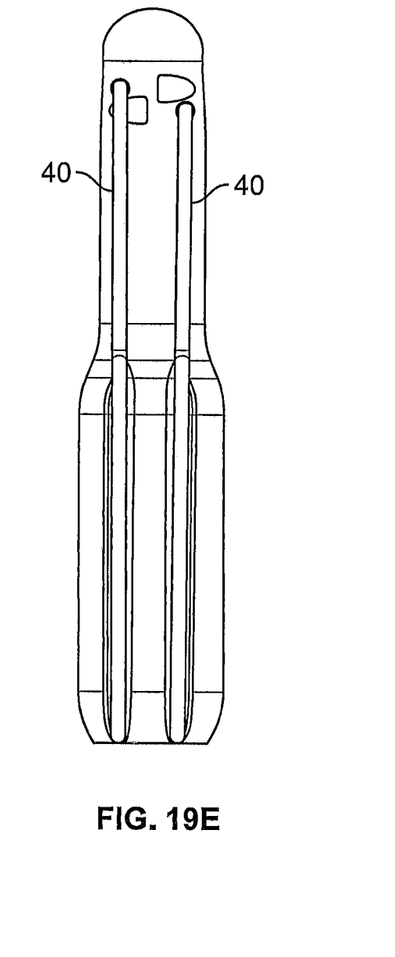
FIG. 19E is a rear view of the tip.
Figure 19F:
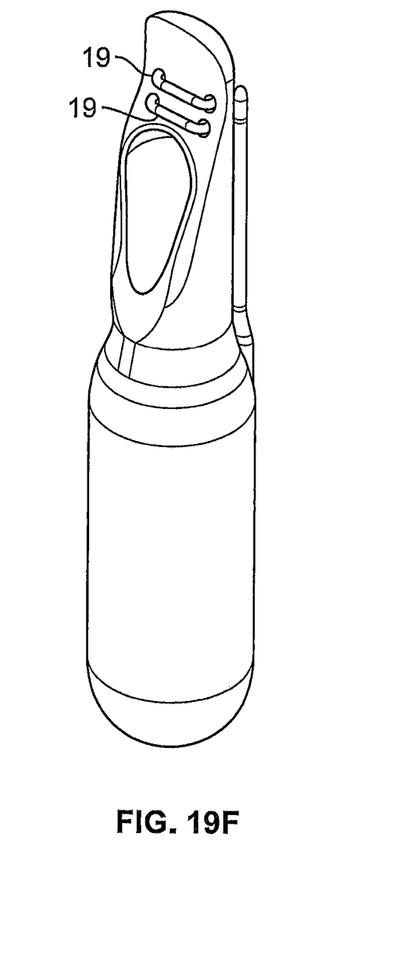
FIG. 19F is a perspective view showing a working bottom portion of the tip.

FIGS. 19A-19F illustrate illustrates multiple views of the tip at various angle positions. FIG. 19A is an end view of the tip. FIG. 19B is a bottom view of the tip. FIG. 19C is another end view of the tip. FIG. 19D is a side elevational view of the tip. FIG. 19E is a rear view of the tip, similar to the view of FIG. 18. FIG. 19F is a semi perspective view showing a working bottom aspect of the tip of the invention.

What is claimed is:

1. An electrosurgical device comprising:
    a distal end region;
    a proximal end region;
    a malleable or curved shaft extending between said distal end region and said proximal end region;
    a hand-piece disposed at said proximal end region;
    a surgical tip positioned at said distal end region, said surgical tip having a rounded and tapered front area;
    a microdebrider;
    a plurality of radio frequency electrodes positioned at a bottom part of said distal end region;
    a plurality of bipolar electrodes positioned at said bottom part of said distal end region;
    said plurality of radio frequency electrodes and said plurality of bipolar electrodes being spaced from said rounded and tapered front area; and
    a heat-resistant upper surface disposed at a top area of said surgical tip, said heat-resistant upper surface separating said plurality of radio frequency electrodes and said plurality of bipolar electrodes from overlying surface tissue;
    wherein said plurality of radio frequency electrodes comprise a first radio frequency electrode extending laterally and longitudinally along a first side of said microdebrider and a second radio frequency electrode extending laterally and longitudinally along a second side of said microdebrider;
    wherein said plurality of bipolar electrodes comprise a first bipolar electrode extending at an angle to a front part of said first radio frequency electrode laterally or just distal to a tip of said microdebrider and a second bipolar electrode extending at an angle to a front part of said second radio frequency electrode laterally or just distal to said tip of said microdebrider;
    wherein said first bipolar electrode and said second bipolar electrode are positioned at said rounded and tapered front area of said surgical tip;
    wherein said first radio frequency electrode and said first bipolar electrode form a first combined unitary electrode assembly;
    wherein said second radio frequency electrode and said second bipolar electrode form a second combined unitary electrode assembly; and
    wherein said first combined unitary electrode assembly and said second combined unitary electrode assembly surround a front portion of said microdebrider.

2. The electrosurgical device according to claim 1, wherein during operation of each of said first and second combined unitary electrode assembly, a same electrical current feed is used to operate said first and second radio frequency electrode and said first and second bipolar electrode.

3. The electrosurgical device according to claim 1, wherein
    said first radio frequency electrode extends along a longitudinal axis of the device and is disposed above said microdebrider;
    said second radio frequency electrode extends along said longitudinal axis of the device and is disposed above said microdebrider;
    said first bipolar electrode extends at an angle to said front part of said first radio frequency electrode in a downward direction; and said second bipolar electrode extends at an angle to said front part of said second radio frequency electrode in said downward direction;

so that said first bipolar electrode and said second bipolar electrode are positioned at said rounded and tapered front area of said surgical tip to allow for precise visualization and targeted cauterization of affected vessels with less trauma to a surrounding tissue.

\* \* \* \* \*